United States Patent [19]

Rose

[11] 4,213,344
[45] Jul. 22, 1980

[54] METHOD AND APPARATUS FOR PROVIDING DYNAMIC FOCUSSING AND BEAM STEERING IN AN ULTRASONIC APPARATUS

[75] Inventor: Joseph L. Rose, Churchville, Pa.

[73] Assignee: Krautkramer-Branson, Incorporated, Stratford, Conn.

[21] Appl. No.: 951,490

[22] Filed: Oct. 16, 1978

[51] Int. Cl.³ .............................................. G01N 29/04
[52] U.S. Cl. ........................................ 73/620; 73/642
[58] Field of Search .................. 73/620, 642; 310/335; 340/5 MP

[56] References Cited

U.S. PATENT DOCUMENTS

| | | | |
|---|---|---|---|
| 2,525,873 | 10/1950 | De Lano | 73/642 |
| 3,913,061 | 10/1975 | Green | 340/5 MP |
| 3,937,066 | 2/1976 | Green et al. | 340/5 MP |
| 4,044,273 | 8/1977 | Kanda et al. | 310/335 |
| 4,061,415 | 12/1977 | Taenzer | 73/620 |

*Primary Examiner*—Anthony V. Ciarlante
*Attorney, Agent, or Firm*—Ervin B. Steinberg; Philip J. Feig

[57] ABSTRACT

An acoustic lens having nonuniform cross sectional thickness is disposed in the path of an ultrasonic energy search beam traveling from a transducer probe to an object to be examined. In an alternative embodiment the lens has at least one contoured surface. As the lens undergoes motion in a plane substantially normal to the direction of the search beam, the search beam exhibits a varying focal zone depth and beam path for providing real time ultrasonic scanning of the examined object.

14 Claims, 8 Drawing Figures

METHOD AND APPARATUS FOR PROVIDING DYNAMIC FOCUSSING AND BEAM STEERING IN AN ULTRASONIC APPARATUS

SUMMARY OF THE INVENTION

The present invention concerns a method and apparatus for providing real time dynamic focussing and beam steering of an ultrasonic energy search beam. Specifically, an acoustic lens having a nonuniform thickness and contoured surface is disposed in the path of the search beam traveling from an ultrasonic transducer probe to an object to be examined. The lens is made to undergo motion in a plane substantially normal to the direction of the search beam thereby continually changing the lens characteristics intercepting the search beam in a predetermined manner for changing the path and focal zone length of the search beam.

In ultrasonic pulse-echo testing, for a given transmitter probe and ultrasonic frequency, the ratio of the probe diameter to the wavelength of the search beam traveling through the test object defines the near field focal zone distance and focal zone width. In ultrasonic imaging systems, it is desireable to form the zone width as small as possible for obtaining optimal lateral resolution while concurrently causing the focal zone to occur at different distances from the transducer probe for providing sharp images throughout the cross section of the object being examined. Moreover, it is advantageous to vary the direction of the search beam without moving the transducer probe. To these ends the present invention provides an arrangement for varying the focal zone depth in real time (so-called real time dynamic focussing) and varying the path of the search beam while maintaining the transducer stationary (so-called real time beam steering). In the past a trade off between these variables generally resulted in a compromise between the focal zone depth and the resolution of the imaging system.

A prior solution to the optimization problem has been to use focussing transducer probes in order to increase the depth regions to be examined. Such focussing is realized by means of curved radiators, or using plane radiators in contact with curved lenses. Depending on the shape of the radiator either spherical or cylindrical lenses are used. While the desired focal zone width is achieved, varying of the depth is not achieved.

Alternatively, mirrors have been used in a manner similar to focussing in optics, see U.S. Pat. No. 3,965,455, issued to M. J. Hurwitz, entitled "Focussed Arc Beam Transducer Reflector" as well as rotating mirrors such as described in U.S. Pat. No. 3,992,925 issued to J. R. Perilhou, entitled "Device for Ultrasonic Scanning". In a further arrangement a transducer probe comprising a linear array of juxtaposed elements is energized in a predetermined fashion to electronically create the effect of a focussed search beam. Such electronic focussing while effective, generally requires a control unit or a plurality of delay lines which add to the cost and complexity of the test arrangement. In a still further arrangement, electronic beam steering and lenses are combined to focus a beam as described, for instance, in U.S. Pat. No. 3,936,791, issued to G. Kossoff, entitled to "Linear Array Ultrasonic Transducer".

The concept of varying the focal zone of an ultrasonic search beam in ultrasonic testing is described, for instance, in U.S. Pat. No. 3,310,977, issued to W. C. McGaughey entitled "Ultrasonic Inspection Apparatus Using Variable Focus and Gate." In the patent, a rack and pinion controlled piston varies the pressure of a liquid contacting a resilient diaphragm to vary the shape of the liquid path coupling the search beam from the transducer probe to the diaphragm and hence, to the test object.

The present invention provides a simplified and inexpensive arrangement for varying the focal zone length and directivity of an ultrasonic energy search beam. An acoustic lens having nonuniform thickness, for instance in the shape of a wedge, is disposed in the path of the search beam. The lens is coupled to undergo motion, for instance rotational motion, in a plane substantially normal to the path of the search beam for providing a varying thickness lens intercepting the search beam at predetermined instances of time. Additionally, the lens surface may be contoured for providing different refraction characteristics. A lens having predetermined surface contours for focussing an ultrasonic search beam is described for instance in U.S. Pat. No. 4,044,273, issued to H. Kanda et al, entitled "Ultrasonic Transducer."

The present invention, furthermore, provides a system in which an ultrasonic search beam transmitted either from a transducer or an array of juxtaposed transducer elements can be steered and the depth of focus varied by means of a simple mechanical arrangement. Such an arrangement is of value in real time ultrasonic pulse-echo examination of human bodies or other workpieces. That is, the heretofore employed complex methods of dynamically focussing an ultrasonic search beam in a real time image scanning device has been replaced by an acoustic lens coupled to motive means.

A principal object of the present invention is, therefore, the provision of an acoustic lens undergoing motion in a plane normal to the path of an ultrasonic energy search beam for varying the beam path and/or the focal zone depth of the search beam.

Another object of the invention is the provision of a method and apparatus for providing a dynamically focussed search beam for use in real time ultrasonic apparatus.

Another object of the invention is the provision of a method and apparatus for varying the beam path and/or the focal zone depth of a search beam by rotating an acoustic lens at a constant angular velocity in the path of the search beam.

A further object of the invention is the provision of a method and apparatus for providing steering of an ultrasonic search beam.

Further and still other objects of the present invention will become more clearly apparent when the following description is read in conjunction with the accompanying drawings.

DETAILED DESCRIPTION OF THE INVENTION

Figure 1:
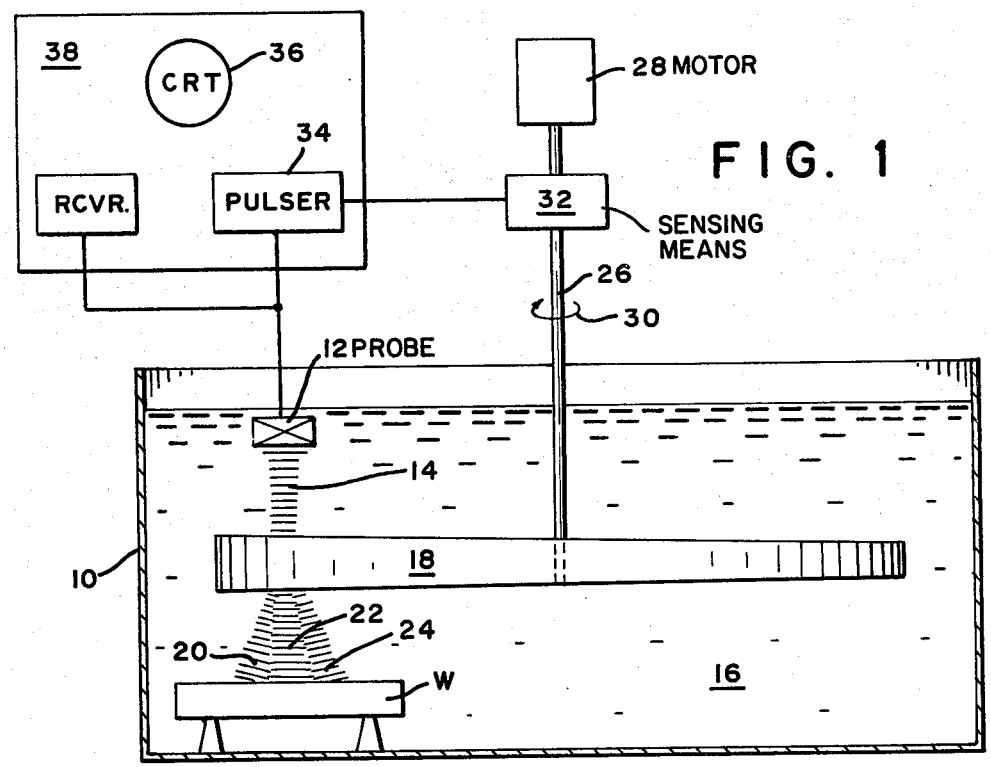
FIG. 1 is a schematic side elevational view of a preferred embodiment of the present invention.
Figure 2:
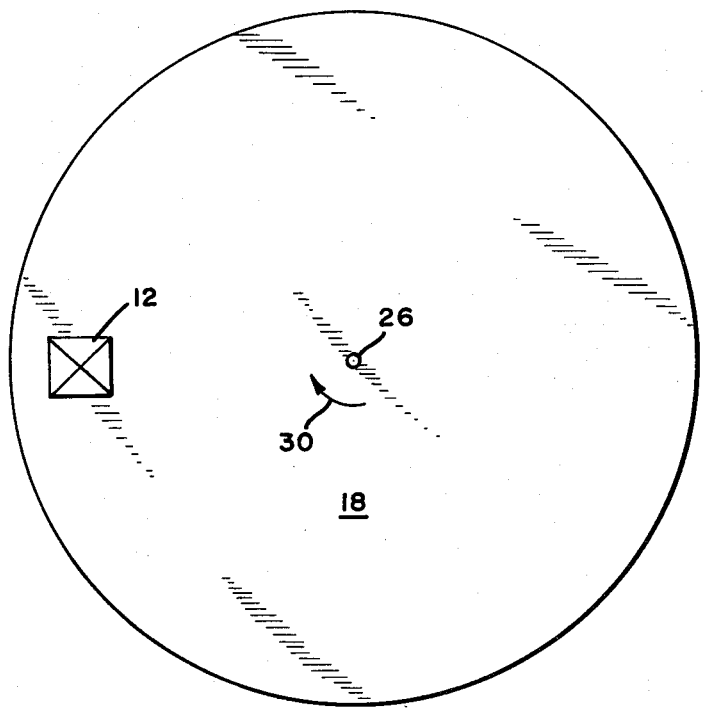
FIG. 2 is a side view of a portion of the arrangement per FIG. 1.
Figure 3:
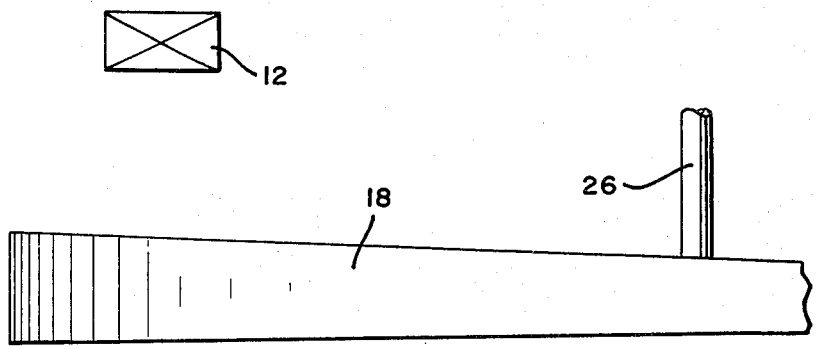
FIG. 3 is a schematic representation of a search beam exhibiting varying focal zone lengths.

Referring now to the figures and FIG. 1 in particular, there is shown a tank 10 and an ultrasonic transducer probe 12 disposed therein for transmitting an ultrasonic search beam 14 through a coupling medium 16, such as water, toward an object W to be examined. The frequency of the transmitted search beam is typically in the range between 0.5 and 10 MHz. The probe 12 is preferably energized in a manner for providing cyclically pulsed search beams such as are used in pulse-echo ultrasonic testing, although continuous wave search beams may also be used in practising the invention. Interposed in the path between the transducer 12 and the test object is a plate 18. The plate 18, an acoustic lens, is dimensioned to exhibit nonuniform thickness for refracting the search beam 14 in a predetermined manner for instance first along path 20, then path 22 and finally path 24 as the plate 18 is rotated by motor 28 about shaft 26 in the direction of arrow 30 as seen in the plan view in FIG. 2. Alternatively, the plate 18 may be dimensioned to change the focal zone length of the search beam. For instance, the search beam wave front may first follow the contour of the solid lines 44 in FIG. 3 for creating a focal zone at region 46, then follow the contour of dotted lines 48 for creating a focal zone at region 50 as the plate 18 undergoes rotation. Rotation of the plate 18, a disk, causes a change of the search beam path or of the focal zone depth or both, thus providing for an examination of the workpiece W at varying locations.

As the plate 18, in the form of a scanning disk, undergoes rotational motion in a plane normal to the path of the search beam, preferably at a uniform speed, the search beam 14 encounters a steadily changing lens thickness, thus causing the beam to exhibit a repetitive pattern of varying beam path and focal zone depth.

Figure 4A:
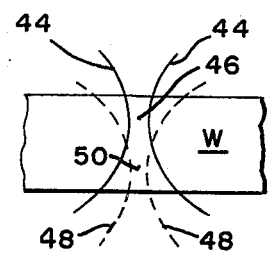
FIG. 4a is a side view of an alternative embodiment of an acoustic lens for practising the invention.
Figure 4A:
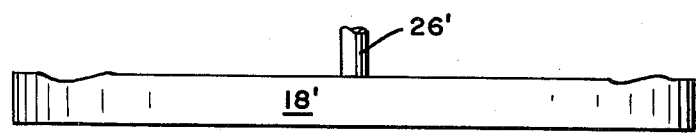
Figure 4B:
FIG. 4b is a side view of a further alternative embodiment of an acoustic lens for practising the invention.
Figure 4C:
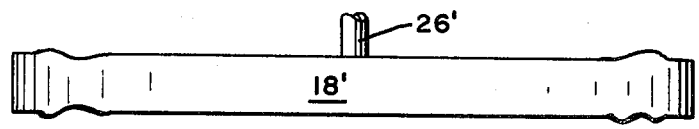
FIG. 4c is a side view of a still further alternative embodiment of an acoustic lens for practising the invention.

In an alternative embodiment a plate 18' may have a contoured groove in the top surface, at a location for intercepting the search beam 14. Alternatively, the plate 18' may have contoured grooves in the bottom surface as shown in FIG. 4b or contoured grooves in both the top and bottom surfaces as shown in FIG. 4c. In a still further modification, not shown, the lens may exhibit varying thickness as well as have one or more contoured grooves. By proper contouring of the surface of plate 18' which acts as an acoustic lens, the search beam 14 is refracted to scan the object to be examined in a predetermined manner. By synchronizing the transmission of the search beam 14, the rotational speed of the motor 28 and the sweep signal on a cathode ray tube, all as known in the art, a real time scanning of the object to be examined can be performed and displayed on the cathode ray tube 36 of an ultrasonic nondestructive test apparatus 38.

Sensing means 32, for instance, a cam and switch, a shaft encoder, or a light reflecting arrangement as shown in U.S. Pat. No. 4,034,744 issued to P. R. Goldberg, entitled "Ultrasonic Scanning System With Video Recorder" coupled to the rotating shaft 26 can provide a trigger signal to the pulser 34 comprising a portion of the ultrasonic nondestructive test apparatus 38 for energizing the probe 12 when the plate 18 is at a desired position to scan the test object. By rotating the plate 18 at a predetermined speed the path of the refracted search beam and the focal zone depth as a function of time is known and used to control the deflection of the beam on the screen of a cathode ray tube 36 to produce a real time image of the test object.

It will be understood that the plate may undergo elliptical as well as circular-rotational motion. Moreover, the plate 18 may exhibit linear motion to affect the dynamic focussing and beam steering effects. It is possible for the transducer 12, which may be a single transducer element or an array of juxtaposed elements, the construction of both as is well known in the art, to undergo motion, preferably linear translatory motion, concurrently with the plate 18 undergoing motion as shown in FIG. 6.

Figure 6:
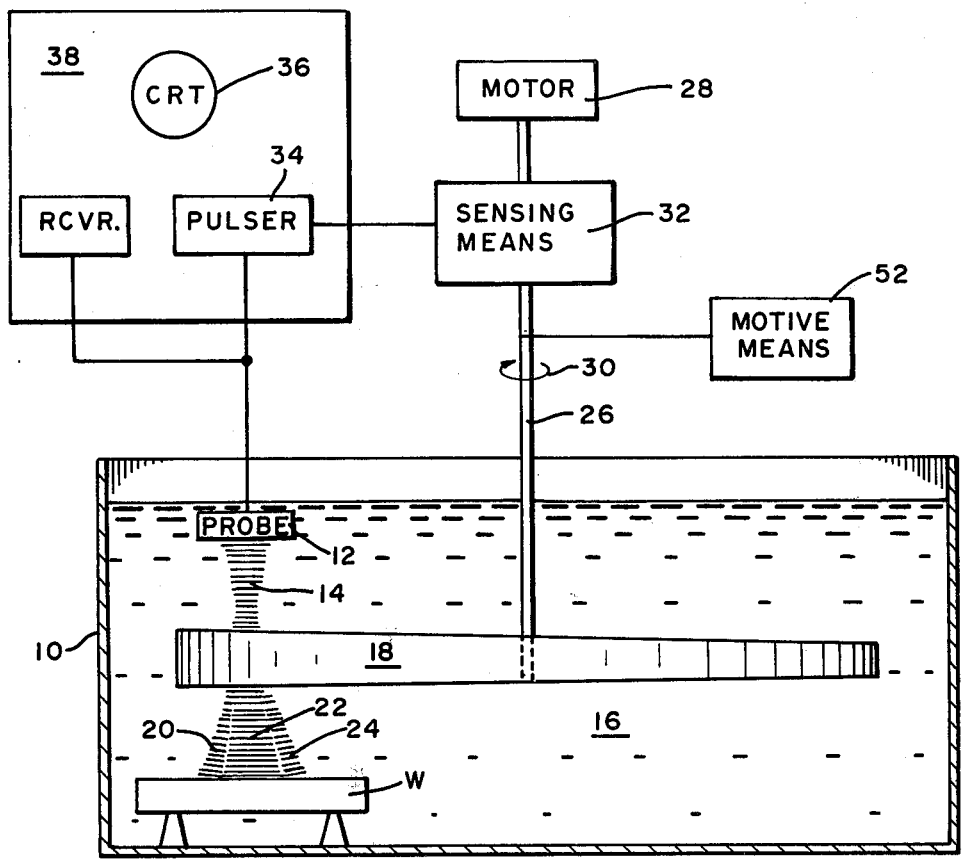
FIG. 6 is a schematic side elevational view of an alternative embodiment of the invention.

In FIG. 6, the arrangement per FIG. 1 is modified to include motive means 52 such as a cam and cam follower, a reciprocating rod or the like, causing the shaft 26 and hence lens 18 to undergo bodily linear translating or elliptical motion depending upon the elements in motive means 52 as is well known to those skilled in the art.

As the disk undergoes motion the effect of an infinite sequence of lenses each of different contour intercepting the search beam in a plane substantially normal to the search beam path is manifest.

Figure 5:
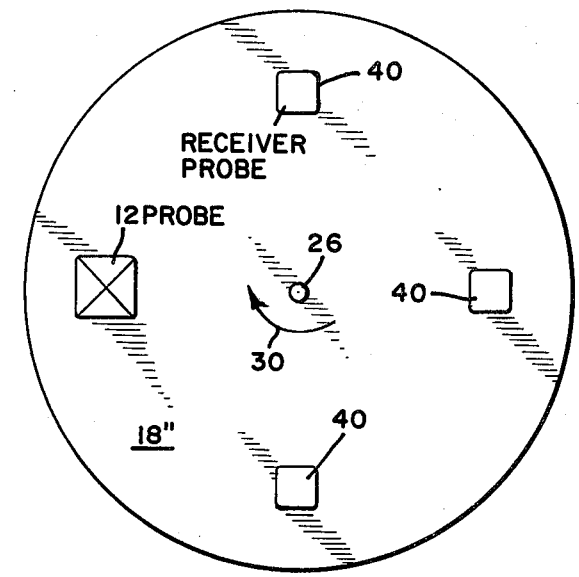
FIG. 5 is a plan view of an alternative embodiment of an acoustic lens for practising the invention.

In a further modification shown in FIG. 5, the plate 18" includes one or more receiver probes 40 (three shown) for receiving back-scattered echo signals and reflected signals from the workpiece. The received echo signals are converted by the receiver probe into electrical signals and conducted via slip rings or the like to the ultrasonic nondestructive test apparatus 38. By analyzing the scatter responsive signals in a manner such as described in U.S. Pat. No. 3,996,791 by L. Niklas et al, entitled "Ultrasonic Test Method and Apparatus Utilizing Scattered Signals" flaw characterization of the defect can be provided. It will be apparent that other combinations of transmitter and receiver probes may be disposed in or in relation with plate 18" to provide flaw characterization analysis.

While a preferred embodiment and several modifications of the present invention have been described and illustrated, it will be apparent to those skilled in the art that further variations and modifications can be made without deviating from the broad principle of the invention which shall be limited solely by the scope of the appended claims.

What is claimed is:

1. An ultrasonic apparatus for changing the path and focal zone length of an ultrasonic energy search beam comprising:

ultrasonic energy transmitting means coupled for transmitting an ultrasonic energy search beam toward an object to be examined;

acoustic lens means interposed in the path of said search beam from said transmitting means to the object, said lens means having a contoured groove surface for changing the focal zone length and the path of said search beam, and motive means coupled to said lens means for causing said search beam responsive to motion of said lens means in a plane substantially normal to the search beam path to change focal zone length and beam path in a predetermined scan pattern to cause a scan of the object portion in the path of said beam.

2. An ultrasonic apparatus as set forth in claim 1, said lens means having a nonuniform thickness.

3. An ultrasonic apparatus as set forth in claim 1, said motion being rotational motion.

4. An ultrasonic apparatus as set forth in claim 3, said rotational motion being at a uniform speed.

5. An ultrasonic apparatus as set forth in claim 1, said lens means being a plate.

6. An ultrasonic apparatus as set forth in claim 1, said transmitting means and the object being at a predetermined fixed distance apart.

7. An ultrasonic apparatus as set forth in claim 1, said transmitting means cyclically transmitting said search beam.

8. An ultrasonic apparatus as set forth in claim 1, said lens means including ultrasonic energy receiving means disposed for receiving echo signals from the object.

9. An ultrasonic apparatus as set forth in claim 1, said ultrasonic energy transmitting means being coupled for undergoing motion relative to the object.

10. A method of changing the path and focal zone of an ultrasonic energy search beam comprising:
transmitting an ultrasonic energy search beam toward an object to be examined;
disposing acoustic lens means having a contoured groove surface in the path of said search beam, and
causing said lens to undergo motion in a plane substantially normal to the path of said search beam for changing the focal zone length and the path of said search beam in a predetermined scan pattern to cause a scan of the object portion in the path of said beam.

11. A method as set forth in claim 10, said lens means having a nonuniform thickness.

12. A method as set forth in claim 10, said lens means being a plate.

13. A method as set forth in claim 10, said motion being rotational motion.

14. A method as set forth in claim 13, said rotational motion being at a uniform speed.

* * * * *